(12) United States Patent
Collins

(10) Patent No.: US 6,799,574 B1
(45) Date of Patent: Oct. 5, 2004

(54) MEDICO-SURGICAL TUBE

(75) Inventor: Michael Norman Collins, Folkestone (GB)

(73) Assignee: Smiths Group PLC, London (GB)

( * ) Notice: Subject to any disclaimer, the term of this patent is extended or adjusted under 35 U.S.C. 154(b) by 160 days.

(21) Appl. No.: 10/031,608

(22) PCT Filed: Aug. 7, 2000

(86) PCT No.: PCT/GB00/03044

§ 371 (c)(1),
(2), (4) Date: Jan. 22, 2002

(87) PCT Pub. No.: WO01/13979

PCT Pub. Date: Mar. 1, 2001

(30) Foreign Application Priority Data

Aug. 26, 1999 (GB) .............................................. 9920098

(51) Int. Cl.[7] .............................................. A61M 16/00
(52) U.S. Cl. ............................ 128/207.15; 128/207.14; 128/200.26
(58) Field of Search ...................... 128/207.14, 207.15, 128/200.26; 604/96.01

(56) References Cited

U.S. PATENT DOCUMENTS

| | | | | |
|---|---|---|---|---|
| 4,315,505 A | * | 2/1982 | Crandall et al. ........ | 128/200.26 |
| 4,607,635 A | * | 8/1986 | Heyden ................. | 128/207.15 |
| 4,674,495 A | * | 6/1987 | Orr ...................... | 128/207.14 |
| 4,751,924 A | * | 6/1988 | Hammerschmidt et al. ...... | 128/207.15 |
| 5,067,496 A | * | 11/1991 | Eisele .................... | 128/207.15 |
| 5,372,131 A | * | 12/1994 | Heinen, Jr. ............ | 128/207.15 |
| 5,497,768 A | * | 3/1996 | Lomholt ................ | 128/207.16 |
| 5,520,175 A | * | 5/1996 | Fry ........................ | 128/207.15 |
| 5,588,424 A | * | 12/1996 | Insler et al. .......... | 128/207.15 |
| 5,682,880 A | * | 11/1997 | Brain .................... | 128/207.15 |
| 6,053,167 A | * | 4/2000 | Waldeck ................ | 128/207.14 |
| 6,148,818 A | * | 11/2000 | Pagan ................... | 128/207.15 |
| 6,460,540 B1 | * | 10/2002 | Klepper ................. | 128/207.14 |

FOREIGN PATENT DOCUMENTS

GB          2335362 A  * 9/1999  ............ 128/207.15

* cited by examiner

Primary Examiner—Henry Bennett
Assistant Examiner—Mital Patel
(74) Attorney, Agent, or Firm—Louis Woo

(57) ABSTRACT

A laryngeal mask airway has a main tubular shaft (1) with a channel (2) of part circular section opening along its external surface. A mask portion (5) is attached to the patient end of the shaft, including a mount (50) and a cuff (60) attached to the mount. A channel (55) extends along the mount (50) from the channel (2) in the shaft (1) to the cuff (60). A small-diameter tube (70) opens at one end into the cuff (60) and extends along the channels (55 and 2) in the mount (50) and in the shaft (1). The channel (2) in the shaft (1) mechanically retains the small-diameter tube (70), the tube extending out of the channel through one of several notches (20) spaced along the channel. The tube (70) can be peeled away from the shaft (1) to extend out of one of the other notches (20), so that the shaft can be cut shorter.

12 Claims, 3 Drawing Sheets

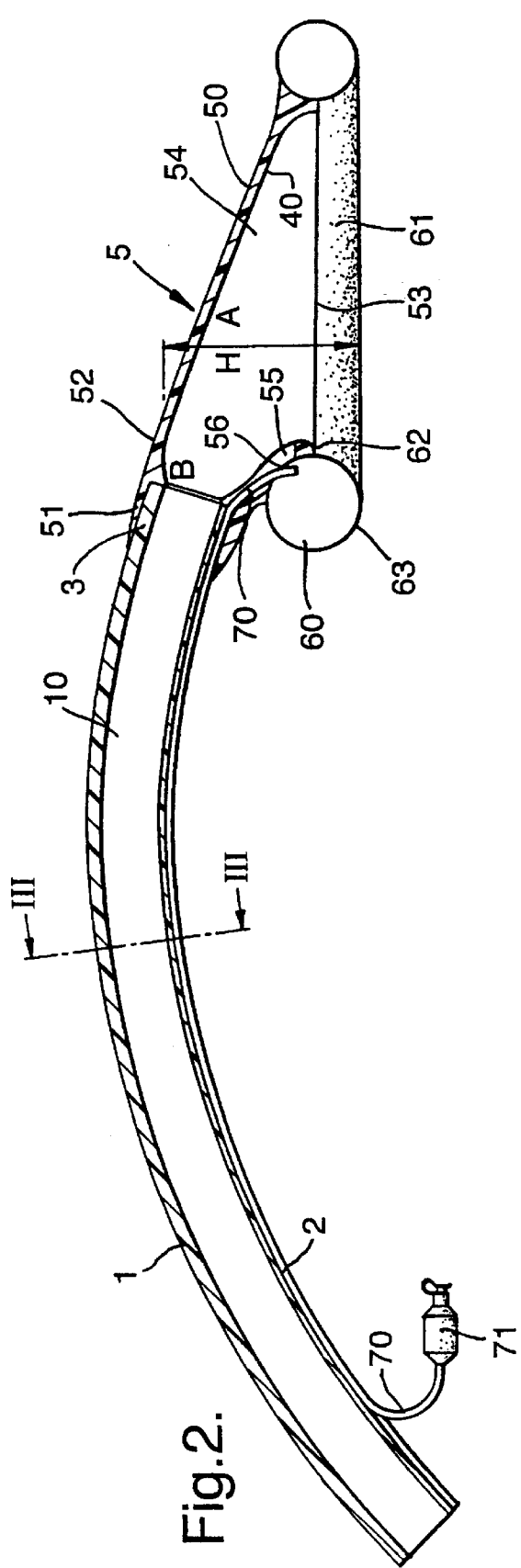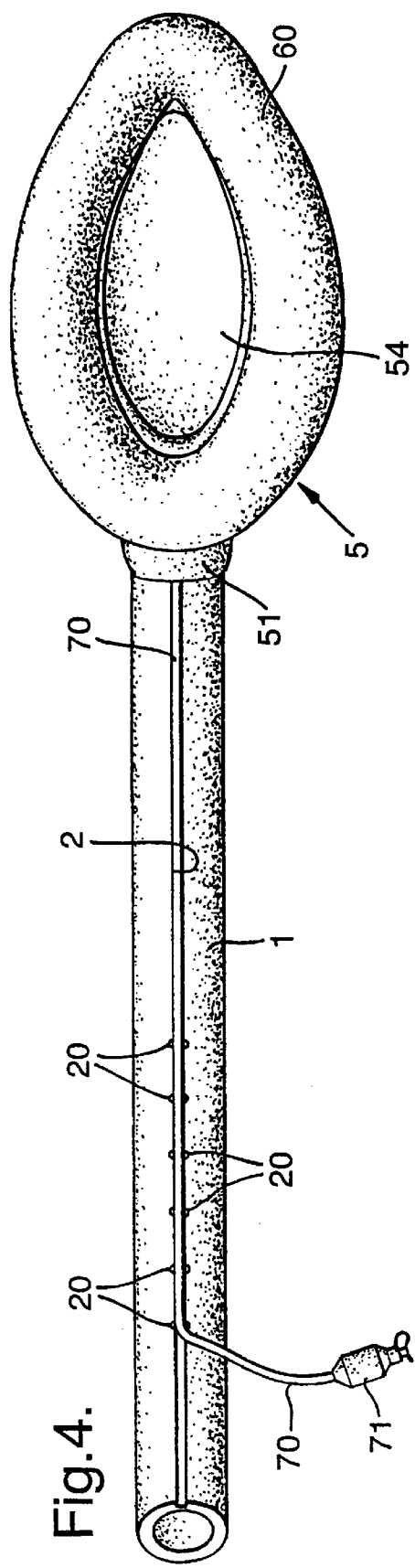

MEDICO-SURGICAL TUBE

Figure 1:
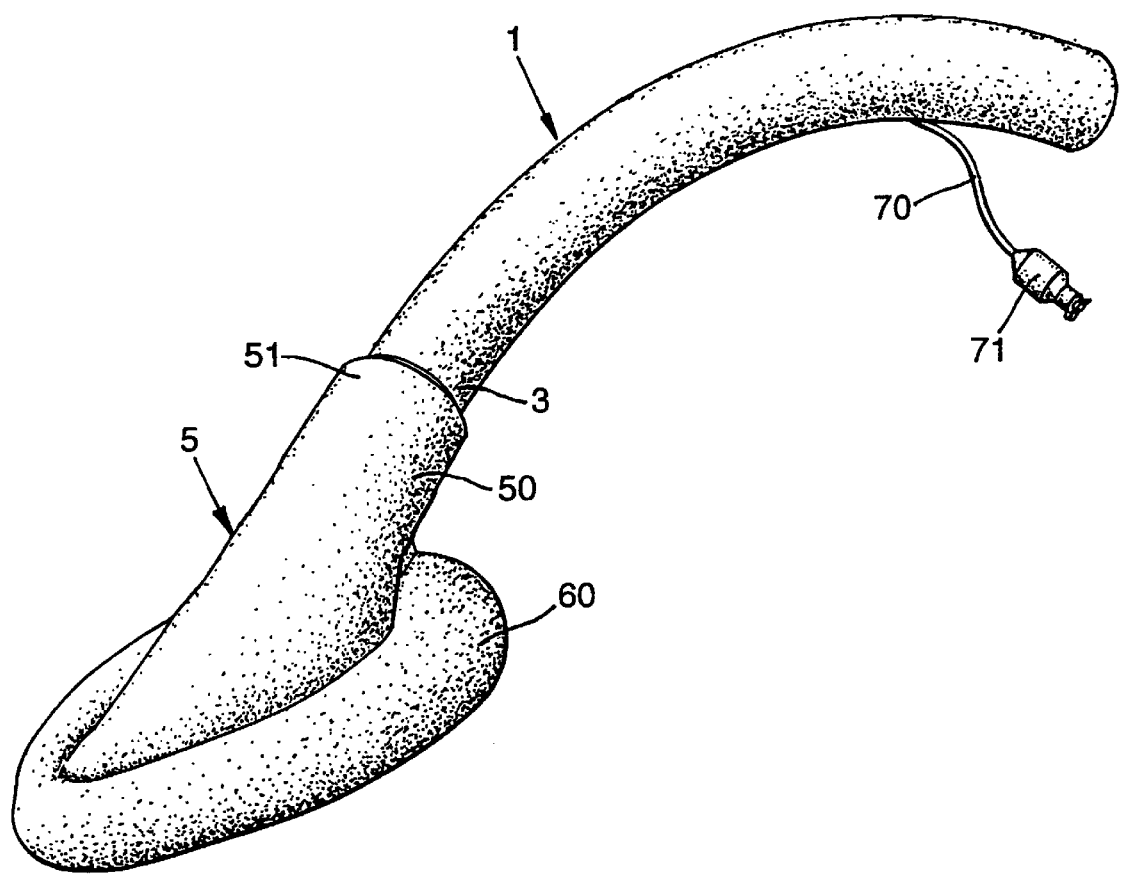

This invention relates to apparatus in the form of a medico-surgical tube having a main tubular shaft with a main lumen and a small-bore minor lumen extending along the wall of the main shaft, the minor lumen being provided at least in part by a small-diameter tube attached along a part of its length with the main shaft.

Laryngeal mask airways are used to ventilate and to supply anesthetic gas to a patient during surgery. Laryngeal mask airways differ from endotracheal tubes, which extend into the trachea and terminate beyond the vocal folds. By contrast, laryngeal mask airways have a tubular shaft opening into the centre of a generally elliptical mask or cuff, which is inflated to seal in the region of the hypopharnyx, at the top of the trachea. The cuff is inflated with air supplied along a small-bore inflation line communicating with the interior of the cuff. The inflation line is not usually attached with the tubular shaft, which can be an inconvenience because it complicates packing and use of the airway. Laryngeal masks are described in, for example: U.S. Pat. No. 5,355,879, U.S. Pat. No. 5,305,743, U.S. Pat. No. 5,297,547, U.S. Pat. No. 5,282,464, GB 2267034, U.S. Pat. No. 5,249,571, U.S. Pat. No. 5,241,956, U.S. Pat. No. 5,303,697, GB 2317830, GB 2249959, GB 2111394, EP 448878, U.S. Pat. No. 4,995,388, GB 2205499, GB 2128561, GB 2298797, GB 2321854, GB 2334215, GB 2323289, GB 2323290, GB 2318735 and GB 2330312.

A problem generally with cuffed medico-surgical tubes, such as laryngeal masks and tracheal tubes is that the users often wish to cut the machine end of the shaft of the tube to length in order not to have an excessive length of tube protruding from the mouth or nose. In tubes having an inflation line attached to the main shaft, the presence of the inflation line limits the extent to which the tube can be cut to length.

It is an object of the present invention to provide alternative medico-surgical apparatus.

According to one aspect of the present invention there is provided apparatus of the above-specified kind, characterised in that the small-diameter tube is attached with the shaft in a manner such that it can be detached from the shaft to reduce the length attached with the shaft.

The shaft may have a channel extending along its external surface, the small-diameter tube being attached with the shaft in the channel. Alternatively, the small-diameter tube may be attached with the shaft by a rupturable bond.

According to another aspect of the present invention there is provided apparatus in the form of a laryngeal mask airway including a tubular shaft with a channel extending along its external surface and a mask portion mounted at the patient end of the shaft, the mask portion having a mount member mounted on the shaft and an inflatable cuff mounted on the mount member such that the cuff can be inflated to seal with surrounding tissue, characterised in that the mount member has a channel extending between the cuff and the channel on the shaft and a small-diameter inflation line tube extending within the channel along the shaft and within the channel in the mount member to communicate with the interior of the cuff.

The channel on the shaft is preferably shaped to retain mechanically the small-diameter tube. Preferably, the channel on the shaft in section is the major part of a circle and it may have a notch or a plurality of notches spaced from one another along the channel to provide a plurality of locations where the small-diameter tube can extend out of the channel. The shaft may be helically reinforced.

According to a further aspect of the present invention there is provide a method of preparing medico-surgical apparatus, the apparatus including a main tubular shaft with a main lumen, an inflatable cuff towards the patient end of the shaft and a small-bore minor lumen extending along the shaft and opening into the cuff, the minor lumen being provided at least in part by a small-diameter tube detachably attached along a part of its length to the shaft, the method including the steps of peeling the small-diameter tube away from the shaft to a desired location and then cutting the machine end of the shaft on the machine side of the desired location to give the shaft a desired length.

Figure 3:
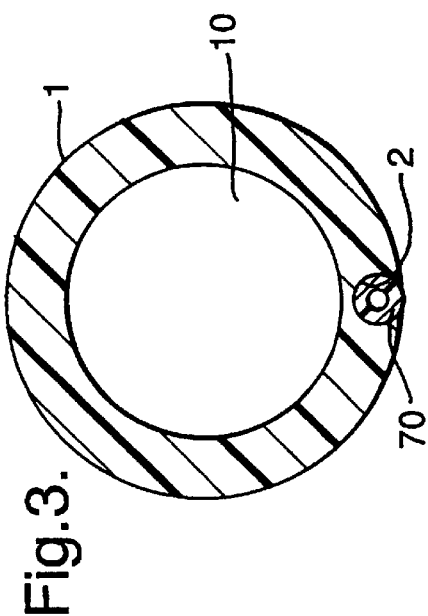
Figure 5:
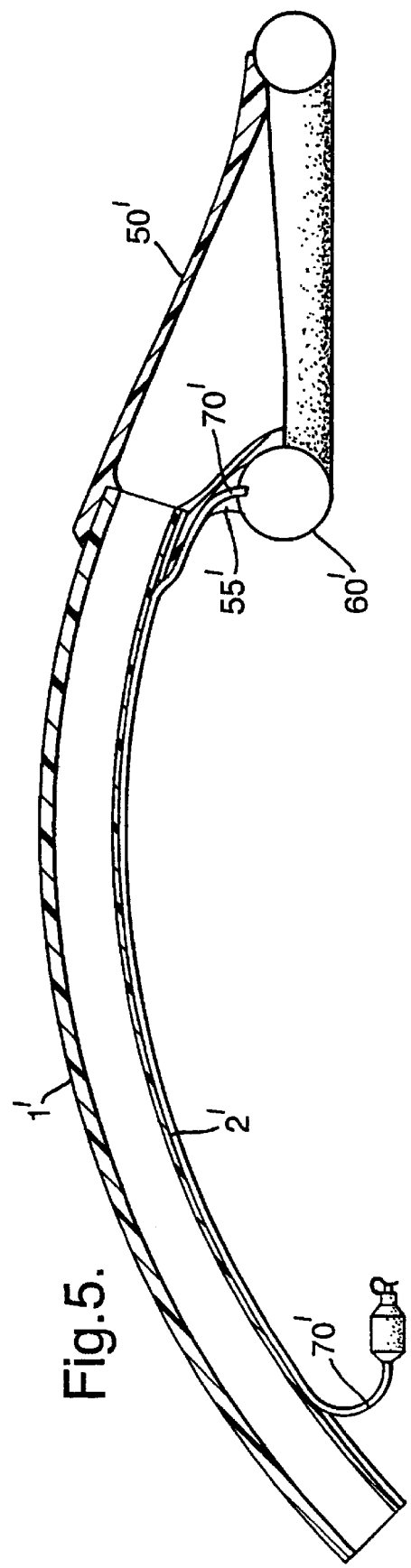

A medico-surgical tube in the form of a laryngeal mask airway according to the present invention, will now be described, by way of example, with reference to the accompanying drawings, in which:

FIG. 1 is a perspective view of the airway;
FIG. 2 is a sectional side elevation view of the airway;
FIG. 3 is a transverse section across the airway along the line III—III of FIG. 2 to an enlarged scale;
FIG. 4 is a view of the airway from below; and
FIG. 5 is a sectional side elevation view of an alternative airway.

With reference to FIGS. 1 to 4, the airway includes a curved tube or shaft 1 of a bendable plastics material having a channel 2 in the form of a groove extending along its length on its outside surface and on the inside of its curve. The shaft 1 is preferably made by extrusion and may be reinforced by means of an embedded helical element, such as of metal or plastics. At its patient end 3, the shaft 1 is attached to a mask portion 5.

The mask portion 5 comprises a mount member 50 of a relatively stiff but compliant plastics material and an inflatable cuff 60 attached to the mount member. The mount member 50 is hollow and of generally shoe shape, having a tubular extension or collar 51 at its upper or posterior side located at the rear, left-hand or machine end of the mount. The patient end 3 of the shaft 1 is bonded into one end of the collar 51. The other end of the collar 51 opens into a central recess or atrium 54 within the mount 50. The internal, anterior surface of the roof 40 of the atrium 54 is arched transversely but is substantially straight, or is slightly concave, along its longitudinal centre line. The roof 40 is uninterrupted by any surface projections or formations that would impede free movement of the epiglottis over the roof. Viewed in plan, the mount 50 is oval with its lower or anterior side 53 lying on a flat plane extending at an angle of about 30° to the axis of the patient end 3 of the collar 51. A channel 55 in the form of a groove extends along the inside of the mount member 50 in line with the groove 2 along the shaft 1 and this opens through a hole 56 into the cuff 60.

The cuff 60 may be of any conventional form, such as described in GB 2323291 or GB 2321854. The cuff 60 is only shown schematically in the drawings but is of annular, elliptical shape, being attached to the forward end surface 53 of the mount member 50 and having a central opening 61 into the atrium 54. The cuff 60 is of a thin, flexible plastics material so that it can be deflated to a low profile for insertion and can be inflated to seal with surrounding tissue when correctly positioned.

The roof 40 of the mount 50 is relatively high compared with previous laryngeal mask airways, especially its central region A and its rear region B adjacent the tubular portion or collar 51. The height H of the atrium ranges from about 2.5 to 3.5 times the internal diameter ID of the shaft 1, or its equivalent where the shaft does not have a circular section— preferably the ratio H/ID is between 2.96 and 3.27. In this way, the atrium 54 has a relatively large volume compared with previous airways. In particular, the ratio of ID³/Volume is in the range 50 to 68 where Volume is the volume of the atrium 54 defined by a plane of the lower, sealing surface of the cuff 61 when inflated, and a vertical, transverse surface through the highest point of the rear region B. For a typical tube having an internal diameter of 8.5 mm, the ratio H/ID might be 3.06 and the ratio of ID³/Volume might be 61.82.

The smallest part of the atrium 54, where the patient end of the collar 51 opens into the atrium, is the part most likely to be blocked by the epiglottis during insertion. The collar 51 positions the patient end 3 of the shaft 1 to the rear of the rear part 62 of the opening 61 and, more particularly, positions it directly above the rear part 63 of the cuff 60 so that it is located as far away as possible from the epiglottis, thereby minimizing the risk of blockage. The large volume of the atrium 54 also ensures that the epiglottis can move freely within the mask, should it enter, so that there is less risk of it catching on the interior of the mask. The present construction avoids the need for any obstruction across the opening of the mask in order to prevent blockage by the epiglottis.

In general, the patient end of the tubular portion 1 is located to the rear of the rear side 62 of the opening 61, that is, on the side towards the machine end of the airway, and is preferably located approximately midway across the width of the sealing cuff. Instead of the tube and mount being separate components, they could be provided by one integral moulded component, with the location where the tubular portion increases in internal diameter being regarded as the patient end of the tubular portion.

The airway also includes an inflation line 70 in the form of a small-diameter flexible plastics tube extending along the groove 2 in the shaft 1, with the patient end of the tube extending along the groove 55 in the mount member 50 and projecting through the hole 56 into the cuff 60. The cuff 60 is sealed with the outside of the inflation line 70 so that it opens into the interior of the cuff. The rear, machine end of the inflation line 70 is attached to a combined inflation indicator balloon and connector 71 of conventional kind. The groove 2 in section forms the major part of a circle, being open on the surface of the shaft through a slit so that the inflation line 70 is retained in the groove mechanically, although it is preferably also bonded into the groove close to the patient end of the shaft 1, such as by means of a solvent or adhesive. A number of lateral notches 20 are spaced from one another along the machine end of the groove 2. The size of the notches 20 is such as to allow the inflation line 70 to extend out of the groove 2 through a notch. The airway is supplied with the inflation line 70 extending out of the groove 2 through the notch 20 closest to the machine end of the shaft 1. If the user wishes to cut the shaft 1 shorter, at a location forwardly of where the inflation line 70 extends from the shaft, he simply pulls the inflation line away from the shaft so that it peels out of the groove 2 to the next notch 20, or to any other notch, thereby reducing the length of the inflation line attached with the shaft. In this way, the inflation line 70 is kept neatly with the shaft along most of the length of the shaft 1 but the shaft can be cut to any desired length. There are other ways in which the inflation line could be attached with the shaft, such as by means of a rupturable adhesive or other bond. It will be appreciated that this form of peelable attachment of a small-bore line could have applications in other tubes having a minor lumen and where it is desirable to be able to alter the length of the small-bore line attached with the main shaft, such as endotracheal tubes.

Securing the inflation line 70 to the shaft 1 along most of its length avoids any loose tube within the patient's mouth and ensures that the inflation indicator and connector 71 are readily accessible outside the mouth. Reliable assembly of the airway is facilitated by this arrangement compared with alternative arrangements employing an extruded small-bore lumen within the wall of the shaft since, in such arrangements, connection needs to be made to both ends of the bore. The present invention can also be used with shafts that are reinforced.

It is not essential that the channel in the mount member extend along its inner surface; it could extend along an outer surface, as shown in FIG. 5, where similar features to those in FIGS. 1 to 4 are given the same numbers with the addition of a prime '. In this arrangement, the groove 55' extends along the outside of the mount member 50' so that the inflation line 70' can run along the groove and open into the cuff 60'.

What is claimed is:

1. Apparatus in the form of a medico-surgical tube having a main tubular shaft with a main lumen, an inflatable cuff and a small-bore minor lumen extending along the wall of the main shaft and opening into the cuff, the minor lumen being provided at least in part by a small-diameter tube attached along a part of the length of said small-diameter tube with the main shaft and bonded at a patient end adjacent said cuff, characterized in that the small-diameter tube is attached with the shaft in a manner such that it said small-diameter tube can be peeled away from the shaft from the machine end of the shaft to reduce the length attached with the shaft.

2. Apparatus according to claim 1, characterized in that the shaft has a channel extending along its external surface, and that the small-diameter tube is attached with the shaft in the channel.

3. Apparatus according to claim 2, characterized in that the channel on the shaft is shaped to retain mechanically the small-diameter tube.

4. Apparatus according to claim 3, characterized in that the channel on the shaft in section is the major part of a circle.

5. Apparatus according to claim 4, characterized in that the channel on the shaft a has notch at a location along the length of the shaft through which the small-diameter tube can extend out of the channel.

6. Apparatus according to claim 3, characterized in that the channel on the shaft has a notch at a location along the length of the shaft through which the small-diameter tube can extend out of the channel.

7. Apparatus according to claim 6, characterized in that the channel on the shaft has a plurality of notches spaced from one another along the channel to provide a plurality of locations where the tube can extend out of the channel.

8. Apparatus according to claim 1, characterized in that the small-diameter tube is attached with the shaft by a rupturable bond.

9. Apparatus according to claim 1, characterized in that the shaft is helically reinforced.

10. Apparatus in the form of a laryngeal mask airway including a tubular shaft with a channel opening along its external surface and a mask portion mounted at the patient end of the shaft the mask portion having a mount member mounted on the shaft and an inflatable cuff mounted on the mount member such that the cuff can be inflated to seal with surrounding tissue, characterized in that the mount member has a channel extending between the cuff and the channel on the shaft and a small-diameter inflation line tube extending within the channel along the shaft and within the channel in the mount member such that one end of the small-diameter tube projects at the machine end of the airway and the other end communicates with the interior of the cuff.

11. Apparatus according to claim 10, characterized in that the channel on the shaft is shaped to retain mechanically the small-diameter tube.

12. A method of preparing medico-surgical apparatus, the apparatus including a main tubular shaft with a main lumen, an inflatable cuff at the patient end of the shaft, and a small-bore minor lumen extending along the shaft and opening into the cuff, characterized in that the minor lumen is provided at least in part by a small-diameter tube secured at a patient end of said tube adjacent said cuff and detachably attached along a part of its length to the shaft and that the method includes the steps of peeling the small-diameter tube away from the machine end of the shaft a desired location and then cutting the machine end of the shaft on the machine side of the desired location to give the shaft a desired length.

* * * * *